United States Patent [19]
Chakrabarti et al.

[11] Patent Number: 4,894,241
[45] Date of Patent: Jan. 16, 1990

[54] HALOPHOR COMPOSITION

[75] Inventors: Paritosh M. Chakrabarti, Pittsburgh, Pa.; Roger A. Crawford, Wadsworth; Robert H. Juda, Akron, both of Ohio

[73] Assignee: PPG Industries, Inc., Pittsburgh, Pa.

[21] Appl. No.: 819,443

[22] Filed: Jan. 16, 1986

[51] Int. Cl.$^4$ ............... A61K 33/36; A61K 59/00; C11D 3/48
[52] U.S. Cl. ............... 424/672; 252/106; 424/722; 424/723
[58] Field of Search ............ 424/150, 672, 722, 723; 252/106

[56] References Cited

U.S. PATENT DOCUMENTS 4,131,556 12/1978 Klopotek et al. ............ 252/106
4,148,884 4/1979 Thorogood ............ 424/150

FOREIGN PATENT DOCUMENTS 2525685 12/1976 Fed. Rep. of Germany ...... 424/150
110778 11/1981 Poland .
2537 11/1889 United Kingdom ............ 424/150
1237911 7/1971 United Kingdom .
1357365 6/1974 United Kingdom .

OTHER PUBLICATIONS

The Merck Index, 10th ed., #35, 3237 and 4121 (1983).
On the Reaction of Dimethylformamide with Bromine, V. A. Petrosyan et al, Armyanshic Journal XXX, No. 6, 1977.
Voltammetric Study of Bromine and Bromides in Dimethylformamide, Siniki et al, Bull. Soc. Chim. de France, 1967, No. 8, 3080–3081.
Solvation Coefficients of Halides, Trihalides and Halogens in Dimethyl–Formamide, Sinicki, Bull., Soc. Chim de France, 1970, No. 4, pp. 1643–1648.
Study of the Local Etching of Gallium Arsenide and Indium Phosphide with a Dimethylformamide Solution of Bromine, Vozmilova et al, Neorganicheskie Materialy, vol. 16, No. 1, 1980, pp. 13–17.
Polarography of Halides in Dimethylformamide, V. Bromine and the Tribromide Ion, Matsui et al, Bull. Chem. Soc. Japan, vol. 43, pp. 2828–2835 (1970).

Primary Examiner—Douglas W. Robinson
Attorney, Agent, or Firm—Irwin M. Stein

[57] ABSTRACT

Halophors of a complex of bromine or iodine, a tertiary amide, e.g., dialkylformamide or dialkyl acetamide, and a halide, e.g., alkali metal or alkaline earth metal bromide or iodide, are described. The alkyl groups of the tertiary amide are typically lower alkyl groups, i.e., groups containing from 1 to 4 carbon atoms. Also described are solid biocidal compositions, e.g., fumigants, of particulate, free-flowing inert amorphous siliceous carrier having at least a biocidal amount of halophor admixed with said carrier.

18 Claims, No Drawings

HALOPHOR COMPOSITION

DESCRIPTION OF THE Invention

The present invention relates to iodine- and/or bromine-containing compositions and the use of such compositions as fumigants and sanitizers. More particularly, the present invention relates to solid, free-flowing biocide compositions od particulate amorphous siliceous carrier having said iodine and/or bromine compositions adsorbed thereon.

The halogens, i.e., chlorine, bromine, and iodine, are recognized as excellent biocidal materials and are used extensively, particularly in the food processing and handling industries, to prevent bacteriological contamination of foodstuffs. Halogen sanitizers are also used in controlling potentially harmful organisms in potable water, swimming pools, hospitals and wherever harmful organisms can present a contamination problem.

In order to utilize the sanitizing property of bromine or iodine and to eliminate or minimize many of the difficulties involved with their use, complexes of bromine or iodine with various materials, such as surfactants, have been suggested. These bromine-containing complexes have been referred to as "bromophors". The iodine-contining complexes are referred to as "iodophors". Surfactants used to prepare such halophors have been selected from a wide variety of materials that include anionic, nonionic and cationic materials. See, for example, British patent specification 1,357,365. The aforesaid patent specification further describes granular bromophor compositions in which the bromophor is sorbed onto a particulate, water-soluble incompletely hydrated inorganic salt which forms stable hydrates.

Brtish patent specification 1,237,911 describes disinfectant compositions comprising a mixture of iodine, an ampholytic organo-amino sulfonate, a nonionic surface active agent and a glycol. This composition is described as being adsorbed onto a silica and mixed with animal feed for controlling the growth of microorganisms within animals such as chickens, turkeys, and pigs. The disinfectant compositions described in British patent specification 1,237,911 are not typical iodophors, i.e., materials that liberate iodine and which exhibit the conventional starch-iodine reaction. The described compositions do not lose iodine even from boiling aqueous solutions but nevertheless are described as having disinfectant or anti-microbial activity, e.g., for in vivo applications.

Fumigation of grain, fruit, vegetables or other food product commodities stored in bulk with bromine compounds such as methyl bromide, ethylene dibromide, and ethylene chlorobromide is performed by applying the bromine compound to the stored commodity in an enclosure which is as gas tight as possible. Low-boiling bromine-containing fumigants, such as methyl bromide, are piped into the enclosure from cylinders of compressed or liquified gas whereas bromine-containing fumigants boiling at temperatures above ambient are sprayed into the area to be treated, e.g., on top of the stored commodity. Preferably the later type fumigant has a specific gravity greater than air and permeates the stored commodity as it falls to the floor of the enlosure.

The present invention provides halophors and halophor compositions which supply a source of bromine and/or iodine. The halophor compositions can be utilized for biocidal, e.g., sanitizing and disinfecting, applications. In those applications, the halophor is commonly added to the aqueous media used to cleanse the surfaces to be cleaned, whereby the halophor releases halogen which forms hypohalite ion in the aqueous medium, which hypohalite serves as the biocidal agent. More particularly, the bromophor compositions may be used as fumigants for grains, vegetables, fruits, seeds and other food products. When used as a fumigant, the halogen, e.g., bromine, of the halophor vaporizes from the halophor, thereby permeating the food products and killing the insects with which it comes into contact.

In accordance with one embodiment of the present invention, there is contemplated a composition comprising a free-flowing, particulate, inert, amorphous siliceous carrier having a biocidal amount of the halophor compositions of the present invention admixed therewith. The siliceous carrier is water-insoluble and has the halophor, i.e., iodophor or bromophor, adsorbed thereon. The halophor comprises a complex of bromine and/or iodine, halide ion, e.g., alkali metal bromide or iodide, or alkaline earth metal bromide, iodide or chloride, and tertiary amides, e.g., formamides, acetamides, or propionamides.

DETAILED DESCRIPTION OF THE INVENTION

The biocidal compositions contemplated herein comprise a complex of bromine and/or iodine, preferably bromine, alkali metal or alkaline earth metal halide, e.g., sodium bromide, and tertiary amide, e.g., dimethyl formamide. In a particular embodiment, there is contemplated particulate or granular inert water-insoluble amorphous siliceous carrier containing the aforedescribed complex (halophor). Typically, the halophor (bromophor or iodophor) is a liquid at standard conditions of temperature and pressure and, in the aforesaid embodiment, is adsorbed by the siliceous carrier. However, herein described halophors that are normally solid may also be used alone or admixed with the siliceous carrier. The aforesaid biocidal compositions can be utilized as germicides, fungicides, insecticides, and for general sanitizing or antiseptic applications. Particularly contemplated herein are halophor, e.g., bromophor, compositions for use as fumigants for fumigation of food commodities and establishments in which food commodities are processed or stored, e.g., enclosures for the storage of grain, or as a soil fumigant for the control of nematodes and root-knot disease. Halophors contemplated for use herein are prepared by combining (1) a tertiary amide, (2) halide ion and (3) elemental bromine or iodine. The tertiary amide can be represented by the following graphic formula:

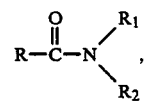

wherein R is selected from the group consisting of hydrogen or $C_1$-$C_2$ alkyl, i.e., methyl or ethyl; $R_1$ is a $C_1$-$C_4$ alkyl, i.e., methyl, ethyl, propyl, or butyl; and $R_2$ is selected from the group consisting of $C_1$-$C_4$ alkyl and phenyl.

More particularly, the tertiary amides contemplated are the N,N-disubstituted products of primary amides; namely, formamide, acetamide and propionamide. Examples of such amides are: N,N-dimethyl formamide, N,N-diethyl formamide, N,N-dimethyl acetamide, N,N- diethyl acetamide, N,N-dipropyl acetamide, N-butyl-N-phenyl acetamide, N,N-dimethyl propionamide, and N,N-diethyl propionamide.

The tertiary amides used herein are preferably normally liquid at standard conditions of temperature and pressure; however, those which are solid at room temperature, e.g., about 20° C., but which have melting points of less than about 100° C. may also be used. Normally solid tertiary amides may be heated to convert them to the liquid state to prepare the halophor complex contemplated herein. The tertiary amides described hereinabove are commercially available or can be readily prepared by one skilled in the art. Typically, the tertiary amides contemplated herein may be prepared by heating the corresponding primary amide, i.e., formamide, acetamide, or propionamide, with the corresponding secondary amine, e.g., dimethyl amine.

The halophors may also be prepared in a suitable organic solvent, such as methanol. The solvent should be capable of dispersing and preferably dissolving the metal halide and tertiary amide; it should be sufficiently volatile so as to be readily removed, e.g., by distillationl, from the halophor; and should be relatively inert, i.e., not react chemically with the tertiary amide or halogen used to prepare the halophor.

The halide ion used in the preparation of the bromophor contemplated herein is provided usually by the bromides or iodides of the alkali metals, sodium, lithium and potassium, and the bromides, iodides or chlorides of calcium and magnesium. Preferably, the aforesaid alkali metal and alkaline earth metal halide is soluble or at least partially soluble in the tertiary amide. Alternatively, anhydrous hydrogen bromide or hydrogen iodide may be used. The halide may be represented by the formula, MX, wherein M is hydrogen, an alkali metal or an alkaline earth metal, and X is iodine or bromine, e.g., MBr, MCl or MI.

The amount of halide used with the tertiary amide can vary. In general, the mole ratio of the halide ion to halogen, e.g., bromide:- bromine ($Br_2$), may vary from 1:1 to 1:12, more usually from 1:1 to 1:3. Preferably, the mole ratio is about 1:2. Depending on the halide (bromide, chloride or iodide) ion and halogen (bromine or iodine) used, the halophor (bromophor or iodophor) may contain one or more of the following halide or interhalide species: $Br_3^-$ and $Br_2$ multiplies thereof, e.g., $Br_5^-$, $Br_7^-$, $Br_9^-$ etc; $Br_2I^-$ and $Br_2$ multiples thereof, e.g., $Br_4I^-$, $Br_6I^-$; $BrI_2^-$ and $Br_2$ or $I_2$ multiples thereof, e.g., $Br_3I_2^-$, $Br_5I_2^-$, $BrI_4^-$ and $BrI_6^-$ etc; and $I_3^-$ and $I_2$ multiples thereof, e.g., $I_5^-$, $I_7^-$, etc.; $Br_2Cl^-$ and $Br_2$ multiples thereof; and $I_2Cl^-$ and $I_2$ multiples thereof.

In accordance with the present invention, the added halide, e.g., alkali metal or alkaline earth metal halide is preferably first admixed with or dissolved (at least partially) in the tertiary amide and halogen, i.e., bromine and/or iodine, introduced into the mixture or solution. While not wishing to be bound by any theory, it is believed that halogen so introduced reacts with the alkali metal halide to form perhalo species rather than reacting with the tertiary amide, thereby providing significant quantities of available halogen, e.g., bromine, in the halophor, i.e., halogen available for biocidal applications. In a preferred embodiment, the amide and halide, e.g., sodium or lithium bromide, are substantially free of water, i.e., contains not more than about 5 weight percent water. Most preferably, the system is substantially anhydrous, which it is believed leads to enhanced stability of the halophor prepared in accordance with the present process.

Halphors described herein can be readily produced by combining the tertiaryamide, added halide, e.g., alkali metal halide, and bromine (and/or iodine) under suitable complexing conditions. For bromophors, it is preferred that liquid bromine be combined with a mixture, e.g., solution, or liquid tertiary amide and the added halide. The reaction between liquid bromine and the amide-halide liquid mixture is generally highly exothermic and hence the reaction mixture should be vigorously stirred and cooled if necessary as the bromine is added slowly. It is generally advisable to maintain the temperature of the reaction mixture from about 25° C. to about 55° C., more usually between 40° C. and about 50° C., for best results, although temporary temperature excursions outside such range will yield satisfactory results as long as temperatures at which the halogen reacts irreversibly with the amide are avoided for extended periods of time. As described, the halophor is preferably prepared in the substantial absence of water, i.e., either added water or water present in the reactants, for enhanced stability of the halophor. Small amounts of water, e.g., from 1 to 5 weight percent, basis the halophor complex, may be tolerated.

The amount of halogen, e.g., bromine, complexed with the amide-halide mixture may vary. Usually the amount of halogen present in the halophor as elemental halogen, e.g., $Br_2$ or $I_2$, will vary from about 10 to about 50, e.g., 25 to 40, weight percent.

In addition, stabilizers, such as acids that are stable under the conditions of use, may be added to the halophor. Some acids that have been suggested for use as stabilizers for halophors, e.g., bromophors, are hydrochloric acid, hydrobromic acid, phosphoric acid, and acetic acid.

The siliceous carrier is, in accordance with a preferred embodiment of the present invention, admixed with sufficient of the halophor to provide at least a biocidal, e.g., insecticidal, amount of the halophor, e.g., bromophor, thereon. A biocidal amount is that amount of halophor that is sufficient to liberate a toxic dosage of elemental bromine and/or iodine, i.e., a dosage sufficient to kill at least 99 percent of the biologic population exposed thereto. Typically, an insecticidal amount is a dosage that results in the killing of at least 99 percent of the biologic population, i.e., the insect population, after their exposure for 24 hours at ambient pressure and a temperature of 25° C. to the halogen(s) liberated from the halophor.

The carrier for the halophor is an inert particulate amorphous siliceous material which is free-flowing and water-insoluble, i.e., has a water solubility at 20° C. of less than 0.5 grams per liter. The siliceous material is chemically inert with respect to the halophor admixed therewith, e.g., the siliceous carrier does not react chemically with the halophor.

The particulate siliceous carrier is of such size as is suitable for the intended use of the herein described halophor composition as a biocidal agent. The particles, for practical purposes, are generally in the range of from 10 to 400 mesh (U.S. Standard Screen), i.e., in the size range of between $-10$ and $+400$ mesh, usually $-12$ or $-14$, $+325$ mesh. The siliceous carrier will typically have an oil absorption of between about 75 and 350 milliliters of dibutyl phthalate per 100 grams of silica. Oil absorption values can be obtained using a method like that described in ASTM D2414-65. For most applications, the oil absorption of the siliceous carrier will be between about 150 and 300 milliliters/100 grams.

The siliceous carrier can be a synthetic amorphous silica or naturally occurring silica- or silicate-containing minerals. Exemplary of synthetic amorphous silicas that may be used as the carrier are precipitated silicas, fumed silicas and silica gels, including hydrogels and xerogels. The aforesaid subcategories of synthetic amorphous silicas refer generally to the method of their preparation. Precipitated silicas are prepared by mixing an alkali metal silicate, e.g., sodium silicate, and a mineral acid, e.g., hydrochloric acid, sulfuric acid or carbonic acid, to cause precipitation of very fine silica particles which are washed free of residual alkali metal salts and dried. Precipitated silicas may be prepared by the methods described in U.S. Pat. No. 2,940,830. Fumed silicas are generally prepared by the flame-hydrolysis of silicon tetrachloride to form a fine silica and by-product hydrochloric acid. Silica gel may be prepared by mixing an alkali metal silicate, e.g., sodium silicate, with a mineral acid at a pH and silica concentration such that a gelatinous precipitate (hydrogel) is formed. The hydrogel can then be washed to remove electrolytes either before or after drying, e.g., spray drying. When the hydrogel is dehydrated, a xerogel is formed. This may be accomplished by replacing the hydrogel water prior to the drying step with a readily volatile material, e.g., an alcohol.

Precipitated silica particularly useful as a carrier for the halophor described herein is material having a BET surface area of between about 130 and about 180 square meters per gram, an oil absorption of between 200 and 270, e.g., between about 230 and 260, milliliters of dibutyl phthalate per 100 grams of silica, a water absorption of between about 160 and 180 milliliters per 100 grams of silica, a median agglomerate particle size of between about 6 and 15, preferably between 8 and 12, microns (micrometers), as measured by a Coulter counter, and a specific volume of at least 3.5 cubic centimeters per gram, e.g., 3.5–4.7 $cm^3/g$, when compacted with an applied pressure of 17 pounds per square inch (psi) (117 kPa).

Such particularly useful precipitated silica may be prepared by (a) establishing an alkali metal silicate, e.g., sodium silicate, aqueous solution having an alkali metal oxide concentration of from about 5.6 to 7.2 grams per liter and a temperature of between about 190° F. (88° C.) and 198° F. (92° C.), (b) slowly adding from 2 to 5 times the original amount of alkali metal silicate to the aqueous solution while simultaneously acidifying the aqueous solution at a rate to maintain the alkali metal oxide concentration therein substantially constant, (c) adding further acidifying agent to the resulting slurry until the pH is from 8 to 9, (d) ageing the slurry at between 188° F. (87° C.) and about 198° F. (92° C.) for from 15 to 90 minutes, (e) adding additional acidifying agent to the aged slurry until the pH is from 4.0 to 4.7 and (f) separating (from the slurry), washing and drying the silica product.

Also contemplated for use as the siliceous carrier are naturally occuring silica- or silicate-containing minerals. These materials are rich in hydrated silicates of aluminum or mangesium and include such clays as montmorillonite, attapulgite, kaolinite, talc, bentoniate, and Fuller's earth, diatomaceous earth, naturally occurring amorphous aluminum silicate (zeolites) and the synthetic zeolites which are an amorphous combination of precipitated alumina and silica. Also contemplated for use as a carrier herein are precipitated calcium silicates, which include synthetic silicas containing small amounts, e.g., 1 to 10 percent, of calcium, calculated as calcium oxide. The above-described synthetic siliceous materials are generally commercially available or can be prepared by techniques known in the art.

The particulate halophor compositions of the present invention can be readily produced by admixing at least one siliceous carrier with the halophor, e.g., liquid bromophor, under conditions designed to obtain a homogeneous mixture. Liquid halophors can be applied to the particulate siliceous carrier by spraying, preferably while the siliceous carrier is stirred or tumbled, to achieve uniform distribution of the halophor on the carrier. Alternatively, the liquid halophor can be poured onto the granular carrier and the mixture thereafter stirred. Halophors that are normally solid or very viscous can be heated slightly to place them in a free-flowing liquid form for making the particulate halophor composition. Generally, it is preferred to maintain the halophor at temperatures of 55° C. or less to prevent irreversible reaction of the halogen, e.g., bromine, with the tertiary amide.

The amount of bromophor or iodophor admixed with the siliceous carrier may vary widely and may be up to that amount which causes the carrier to lose its free-flowing property, i.e., up to the maximum adsorptivity of the siliceous carrier utilized. Hence, the maximum amount of halophor that can be sorbed by the siliceous carrier will be a function of the adsorbtivity of the carrier. A measure of a siliceous carrier's adsorbtivity is its oil absorption. The higher the oil absorption value for a particular siliceous carrier—the greater is the amount of halophor that can be retained by the carrier and still remain free-flowing.

The amount of bromophor or iodophor sorbed onto the siliceous carrier is advisedly selected to provide a free-flowing, granular halophor composition containing at least a biocidal amount of available bromine and/or iodine (or bromiodide). Since the amount of iodine or bromine required for biocidal activity will vary with the end use, e.g., fumigant, santitizer, or disinfectant, the quantity of halophor sorbed onto the carrier may likewise vary and will also depend on the amount of halogen, i.e., bromine and/or iodine present in the halophor available for the particular biocidal application.

It is contemplated that the siliceous carrier, depending on its adsorbtivity, may contain from about 1 to about 80 weight percent of the halophor, basis the weight of the siliceous carrier, e.g., between about 5 and 75 or 10 40, weight percent of halophor. For some applications between about 1 and 35 parts by weight of halophor per 100 parts by weight of the siliceous carrier may be sufficient to provide the biocidal, e.g., the insecticidal, amount of available bromine or iodine.

It is contemplated that more than one amorphous, siliceous carrier may be used to prepare the particulate halophor compositions of the present invention. Thus mixtures of siliceous carriers may be used. It is further contemplated that particulate halophor compositions containing high levels of halophor (in the form of a masterbatch) may be prepared with highly absorptive siliceous carrier(s) and subsequently diluted with other chemically inert solid diluents, e.g., less absorptive (and perhaps less costly) siliceous carriers, clays, and inorganic, preferably water soluble salts. Such particulate halophor masterbatch compositions may contain from about 30 to about 80, e.g., 50 to 75, weight percent halophor. Inorganic salts contemplated are alkali metal sulfates, phosphates, (orthophosphates and polyphosphates) carbonates and chlorides. The salts of sodium and potassium are preferred for most applications. Preferably, the salts are used in their anhydrous form.

The compositions of the present invention are more particularly described in the following Examples which are intended as illustrative only since numerous modifications and variations therein will be apparent to those skilled in the art.

While the present invention has been illustrated by the preparation of bromophor compositions utilizing a precipitated silica carrier and dimethyl formamide or dimethyl acetamide as the tertiary amide, similar results are expected using bromophors prepared with other of the described tertiary amides and using other siliceous carriers.

EXAMPLE I

A reaction flask was charged with 66.8 grams (0.92 mole) of dimethyl formamide and then 33.2 grams (0.38 mole) of lithium bromide was added to the flask over thirty minutes. The temperature of the contents of the flask rose from room temperature (about 18° C.) to 62° C. After the lithium bromide had dissolved in the dimethyl formamide and the temperature of the contents of the flask cooled to 40° C. with an ice bath, 61.3 grams (19.8 milliliters) (0.38 mole) of bromine ($Br_2$) were added slowly with cooling and stirring over thirty minutes to the flask. Thereafter, the reaction mixture was stirred an additional thirty minutes and allowed to cool to 30° C. The bromophor comprised 41.4 weight percent dimethylformamide, 20.6 weight percent lithium bromide and 38.0 weight percent of added bromine. Of the 38.0 weight percent bromine added to the reaction mixture to form the bromophor, 35.4 weight percent was retained in an available form initially.

20.4 grams of the aforesaid bromophor was mixed slowly over 10-15 minutes with stirring at room temperature (about 18° C.) with 10 grams of free-flowing amorphous, precipitated silica having the following typical physical properties: Surface area—140 to 160 square meters per gram; oil absorption—160-220 milliliters; and pH—6.5 to 7.3. The silica remained free-flowing. The silica-bromophor composition of which 67.1 weight percent was the bromophor, was stored in a glass bottle at 30° C. for 16 weeks, after which the test was terminated. Periodically, a sample of the composition was removed and tested by thiosulfate titration for the amount of available bromine remaining in the sample. Results are tabulated in Table I.

TABLE I

| Time, Wks. | Wt. % Available Bromine | Time, Wks. | Wt. % Available Bromine |
| --- | --- | --- | --- |
| Start | 22.8* | 6 | 22.6 |
| 3 Days | 22.8 | 7 | 22.8 |
| 1 | 21.5 | 8 | 22.7 |
| 2 | 22.6 | 9 | 22.5 |
| 3 | 23.2 | 10 | 21.6 |
| 4 | 22.8 | 12 | 22.2 |
| 5 | 23.2 | 16 | 22.4 |

*Theoretical amount of available bromine in the silica-bromophor composition is 23.7 weight percent (.671 × 35.4).

The data of Table I show that the composition of Example 1 remain relatively stable over 16 weeks—the amount of available bromine at that time being substantially the same as the amount of bromine available when the composition was made.

EXAMPLE 2

The bromophor of Example 1 was also stored in a glass bottle at 30° C. for 16 weeks and tested periodically for available bromine. Results are tabulated in Table II.

EXAMPLE 3

The procedure for preparing the bromphor of Example 1 was followed using N,N-dimethylacetamide as the tertiary amide. The amounts (by weight) of the reactants used were the same as in Example 1. The temperature of the contents of the reaction flask rose from room temperature (about 18° C.) to 60° C. during addition of the lithium bromide. About 10% of the lithium bromide did not dissolve in the acetamide. The reaction flask was cooled to 35° C. and the bromine added with cooling over a one hour period. The contents of the flask were then stirred for an additional 3½ hours, of which one hour was at 40° C. The resulting bromophor was cooled to 30° C. and tested for available bromine over 16 weeks as described in Example I. Results are tabulated in Table II.

TABLE II

| Time, Wks. | Wt. % Available Bromine Example No. 2 | Wt. % Available Bromine Example No. 3 | Time, Wks. | Wt. % Available Bromine Example No. 2 | Wt. % Available Bromine Example No. 3 |
| --- | --- | --- | --- | --- | --- |
| Start | 35.4 | 36.1 | 8 | 35.2 | 35.6 |
| 3 Days | 35.5 | 36.0 | 9 | 36.3 | 35.8 |
| 1 | 34.9 | 35.0 | 10 | 35.6 | 36.0 |
| 2 | 35.2 | 35.0 | 11 | 36.1 | 36.6 |
| 3 | 35.2 | 35.3 | 12 | 35.6 | 35.6 |
| 4 | 35.2 | 35.4 | 13 | 36.2 | 35.4 |
| 5 | 35.2 | 35.4 | 14 | 35.8 | 33.8 |
| 6 | 35.3 | 35.5 | 15 | 34.6 | 35.4 |
| 7 | 35.2 | 35.6 | 16 | 35.6 | 35.3 |

The data of Table II show that the bromophors of Examples 2 and 3 are relatively stable at 30° C. over the 16 week test period.

EXAMPLE 4

Run A

The procedure of Example 1 was followed using 84.0 grams of N,N-dimethylformamide, 16.0 grams of lithium bromide and 61.3 grams (19.8 ml) of bromine ($Br_2$). The bromine was added with cooling over 20 minutes. The temperature of the contents of the reaction flask ranged from 41°-46° C., except for one cooling cycle to 35° C., during addition of the bromine. The contents of the flask were then stirred for 15 minutes.

Run B

The procedure of Run A was followed using N,N-dimethylacetamide.

Each of the bromophors prepared in Runs A and B were tested for available bromine over 16 weeks as described in Example 1. Results are tabulated in Table III.

TABLE III

| Time, Wks. | Wt. % Available Bromine Run A | Wt. % Available Bromine Run B | Time, Wks. | Wt. % Available Bromine Run A | Wt. % Available Bromine Run B |
|---|---|---|---|---|---|
| Start | 35.1 | 34.5 | 8 | 30.2 | 29.7 |
| 3 Days | 33.8 | 33.4 | 9 | 30.5 | 29.6 |
| 1 | 33.6 | 32.6 | 10 | 30.4 | 29.8 |
| 2 | 31.6 | 31.6 | 11 | 30.0 | 29.7 |
| 3 | 31.7 | 31.2 | 12 | 29.0 | 28.8 |
| 4 | 32.0 | 31.7 | 13 | 30.1 | 29.2 |
| 5 | 31.6 | 31.3 | 14 | 29.5 | 28.5 |
| 6 | 30.6 | 30.6 | 16 | 29.5 | 28.6 |
| 7 | 31.0 | 30.6 | | | |

The data of Table III show that the bromophors of Example 4 are slightly less than the bromophors of Examples 2 and 3, the former having about half the amount of lithium bromide than the latter.

EXAMPLE 5

Run A

The procedure of Example 1 was followed using 81.1 grams of dimethylformamide, 18.9 grams of sodium bromide and 61.3 grams (19.8 ml) of bromine ($Br_2$). The sodium bromide was admixed with the dimethylformamide and the mixture heated from room temperature (about 18° C.) to about 70° C. to enhance dissolution of the sodium bromide. After stirring for 15 minutes at 70° C., the mixture was cooled to 40° C. and the bromine added with cooling over 20 minutes. The reaction mixture temperature varied from 42° C. to 47° C. during addition of the bromine. The reaction mixture was cooled to 30° C. and tested for available bromine by the procedure described in Example 1. Results are tabulated in Table IV.

Run B

The procedure of Run A was followed except that 78.1 grams of dimethylformamide and 21.9 grams of potassium bromide were used. The reaction temperature varied from 42° C. to 45° C. during addition of the bromine. Results of testing are tabulated in Table IV.

TABLE IV

| Time, Wks. | Wt. % Available Bromine Run A | Wt. % Available Bromine Run B |
|---|---|---|
| Start | 35.6 | 35.3 |
| 3 Days | 34.6 | 35.2 |
| 1 | 34.9 | 35.2 |
| 2 | 34.2 | 33.9 |
| 4 | 33.4 | 33.4 |
| 6 | 32.7 | 33.4 |

The data of Table IV show that sodium bromide and potassium bromide can be used in place of the lithium bromide of Example 1.

EXAMPLE 6

20.6 grams of the bromophor prepared in Example 1 were mixed slowly over 10-15 minutes at room temperature (about 18° C.) with 10 grams of free-flowing, amorphous precipitated silica having the following physical properties: Surface area 170 to 210 square meters per gram; oil absorption—210 to 240 milliliters; pH—6.5 to 7.3; and median particle size—25 micrometers. The silica remained free flowing. The silica-bromophor composition, of which 67.3 weight percent was the bromophor, was stored in a glass bottle at 30° C. for 16 weeks, after which the test was terminated. Periodically, a sample of the composition was removed and tested by thiosulfate titration for available bromine. Results are tabulated in Table V.

TABLE V

| Time, Wks. | Wt. % Available Bromine | Time, Wks. | Wt. % Available Bromine |
|---|---|---|---|
| Start | 23.8 | 6 | 23.5 |
| 3 Days | 23.6 | 7 | 23.0 |
| 1 | 22.1 | 8 | 23.0 |
| 2 | 22.7 | 9 | 23.4 |
| 3 | 23.7 | 10 | 23.5 |
| 4 | 23.6 | 12 | 23.3 |
| 5 | 23.8 | 16 | 23.7 |

The data of Table V show that the bromophor composition of Example 6 is relatively stable over the 16 week test period.

COMPARATIVE EXAMPLE 1

Run A

A reaction flask was charged with 100 grams of N,N-dimethylformamide and 61.3 grams (19.8 ml) of bromine ($Br_2$) added thereto with cooling over a 5-10 minute period. The contents of the reaction flask rose from room temperature (about 18° C.) to 44° C. during addition of the bromine. The reaction mixture was stirred for 20 minutes until the reaction mixture temperature dropped to 30° C. The resulting bromophor was stored in a glass bottle at 30° C. and analyzed periodically for available bromine. Results are tabulated in Table VI.

Run B

The procedure of Run A was followed except that 100 grams of dimethylacetamide and 63.3 grams of bromine were used. The bromine was added with cooling over 45 minutes during which time the reaction mixture temperature ranged between 40° C. and 46° C. The reaction mixture was then stirred for 3½ hours and allowed to cool to 30° C. Results are tabulated in Table VI.

TABLE VI

| Time, Wks. | Wt. % Available Bromine Run A | Wt. % Available Bromine Run B |
|---|---|---|
| Start | 23.3 | 16.8 |
| 3 Days | 22.7 | 10.5 |
| 1 | 21.4 | 10.0 |
| 2 | 20.3 | 9.6 |
| 3 | 20.4 | 9.4 |
| 4 | 18.8 | 9.2* |
| 5 | 18.9 | |
| 6 | 18.2* | |

*Test terminated after this reading.

The data of table VI show that the presence of the alkali metal bromide in the bromophor compositions described in Examples 1-6 promotes the retention of available bromine in the described bromophor.

Although the present invention has been described with reference to specific details of certain embodiments thereof, it is not intended that such detail should be regarded as limitations upon the scope of the invention except as and to the extent that they are included in the accompanying claims.

What is claimed is:

1. A substantially water-free halophor comprising a complex of (a) halogen selected from the group consisting of bromine and iodine, (b) tertiary amide represented by the graphic formula:

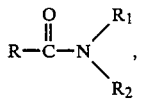

wherein R is selected from the group consisting of hydrogen and $C_1$-$C_2$ alkyl, $R_1$ is a $C_1$-$C_4$ alkyl, and $R_2$ is selected from the group consisting of $C_1$-$C_4$ alkyl and phenyl, and (c) halide represented by the formula, MX, wherein M is alkali metal selected from the group consisting of sodium, potassium and lithium, or alkaline earth metal selected from the group consisting of calcium and magnesium, and X is bromine, chlorine or iodine, the mole ratio of halide to halogen being from about 1:1 to 1:12, and the amount of halogen in the complex being between about 10 and about 50 weight percent.

2. The halophor of claim 1 wherein the halogen is bromine, the tertiary amide is a formamide or acetamide, and the halide is an alkali metal bromide selected from the group consisting of lithium bromide sodium bromide and potassium bromide.

3. The halophor of claim 2 wherein the mole ratio of halide to halogen is from about 1:1 to 1:3 and the amount of halogen in the complex is from about 25 to 40 weight percent.

4. The halophor of claim 3 wherein the tertiary amide is dimethylformamide, diethylformamide, dimethylacetamide or diethylacetamide.

5. The halophor of claim 1 wherein the halogen is bromine, the tertiary amide is a formamide or acetamide, and the halide is a bromide, iodide or chloride of calcium or magnesium.

6. A free flowing substantially water-free particulate halophor composition comprising particulate, inert, amorphous siliceous carrier having adsorbed thereon from about 1 to about 80 weight percent of a complex of (a) halogen selected from the group consisting of bromine and iodine, (b) tertiary amide represented by the graphic formula:

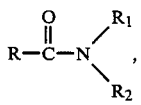

wherein R is selected form the group consisting of hydrogen and $C_1$-$C_2$ alkyl, $R_1$ is a $C_1$-$C_4$ alkyl, and $R_2$ is selected from the group consisting of $C_1$-$C_4$ alkyl and phenyl, and (c) halide represented by the formula, MX, wherein M is alkali metal selected from the group consisting of sodium, potassium and lithium, or alkaline earth metal selected from the group consisting of calcium and magnesium, and X is bromine, chlorine or iodine, the mole ratio of halide to halogen being from about 1:1 to 1:12, and the amount of halogen in the complex being between about 10 and about 50 weight percent.

7. The halophor composition of claim 6 wherein the siliceous carrier is a synthetic amorphous silica amorphous silica or naturally occurring silica- or silicate-containing mineral.

8. The halophor composition of claim 7 wherein the siliceous carrier contains from about 5 to about 75 weight percent of the complex.

9. The halophor composition of claim 8 wherein the halogen is bromine, the tertiary amide is a formamide or acetamide, and the halide is a bromide.

10. The halophor composition of claim 9 wherein the mole ratio of halide to halogen is from about 1:1 to 1:3 and the amount of halogen in the complex is from about 25 to 40 weight percent.

11. The halophor composition of claim 10 wherein the siliceous carrier is precipitated amorphous silica.

12. The halophor composition of claim 11 wherein the tertiary amide is dimethylformamide, diethylformamide, dimethylacetamide or diethylacetamide.

13. A fumigant comprising free flowing, substantially water-free particulate, inert amorphous siliceous carrier having adsorbed thereon an insecticidal amount of a bromophor complex of (a) bromine, (b) tertiary amide represented by the graphic formula:

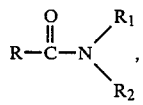

wherein R is selected from the group consisting of hydrogen and $C_1$-$C_2$ alkyl, $R_1$ is a $C_1$-$C_4$ alkyl, and $R_2$ is selected from the group consisting of $C_1$-$C_4$ alkyl and phenyl, and (c) bromide represented by the formula, MBr, wherein M is alkali metal selected from the group consisting of sodium, potassium and lithium, or alkaline earth metal selected from the group consisting of calcium and magnesium, the mole ratio of bromide to bromine being from about 1:1 to 1:12, and the amount of bromine in the complex being between about 10 and about 50 weight percent.

14. The fumigant of claim 13 wherein from about 10 to about 40 weight percent of the siliceous carrier-bromophor complex composition is the bromophor complex.

15. The fumigant of claim 14 wherein the tertiary amide is dimethylformamide, diethylformamide, dimethylacetamide, or diethylacetamide, the bromide is sodium bromide, potassium bromide or lithium bromide, and the mole ratio of bromide to bromine in the complex is between about 1:1 and 1:3.

16. The fumigant of claim 15 wherein the tertiary amide is dimethylformamide.

17. The fumigant of claim 13 wherein the siliceous carrier is precipitated, amorphous silica, the tertiary amide is dimethylformamide, the halide is lithium bromide, sodium bromide, or potassium bromide, and the mole ratio of bromide to bromine is from about 1:1 to 1:3.

18. The fumigant of claim 17 wherein from about 10 to about 40 weight percent of the silceous carrier-bromophor complex composition is the bromophor complex.

* * * * *